US00PP25686P3

(12) United States Plant Patent
Egger

(10) Patent No.: US PP25,686 P3
(45) Date of Patent: Jul. 7, 2015

(54) ×*HEUCHERALLA* PLANT NAMED 'HONEY ROSE'

(50) Latin Name: ×*Heucherella* hybrid
Varietal Denomination: Honey Rose

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 182 days.

(21) Appl. No.: 13/987,661

(22) Filed: Aug. 20, 2013

(65) Prior Publication Data

US 2015/0059035 P1 Feb. 26, 2015

(51) Int. Cl.
*A01H 5/12* (2006.01)

(52) U.S. Cl.
USPC ..... Plt./441

(58) Field of Classification Search
USPC ..... Plt./441
See application file for complete search history.

*Primary Examiner* — June Hwu
(74) *Attorney, Agent, or Firm* — Klarquist Sparkman, LLP

(57) ABSTRACT

A new and distinct ×*Heucherella* plant substantially as shown and described, characterized by palmatifid leaves with prominent sinuses, spring leaves of orange amber with a strong white veil, summer leaves rose amber with a strong white veil, small white flowers on short maroon flower stalks, a medium plant size with multiple crowns, and excellent vigor.

2 Drawing Sheets

Botanical denomination: ×*Heucherella* hybrid.
Variety designation: 'Honey Rose'.

BACKGROUND OF THE INVENTION

The present invention relates to a new and distinct cultivar of ×*Heucherella* and given the cultivar name of 'Honey Rose'. ×*Heucherella* is in the family Saxifragaceae. ×*Heucherella* 'Honey Rose' originated from a controlled cross between *Heuchera* K573-10 (a proprietary unreleased *Heuchera* hybrid), as the seed parent, and *Tiarella* mass pollen from proprietary unreleased *Tiarella* seedlings.

Compared to the seed parent, *Heuchera* K573-10 (unpatented), the new cultivar has leaves that are more lobed and peach to rose colored rather than tan to yellow green.

Compared to the pollen parent, *Tiarella* unknown (unpatented), the new cultivar has peach to rose colored leaves rather than green.

Compared to ×*Heucherella* 'Buttered Rum' (U.S. Plant Pat. No. 25,040), the new cultivar has strongly veiled leaves and a rounder habit.

This new ×*Heucherella* is distinguished by:

1. palmatifid leaves with prominent sinuses,
2. spring leaves of orange amber with a strong white veil,
3. summer leaves rose amber with a strong white veil,
4. small white flowers on short maroon flower stalks,
5. medium plant size with multiple crowns, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a six-month-old ×*Heucherella* 'Honey Rose' growing in a one gallon container in a cool greenhouse in early May Canby, Oreg.

FIG. 2 shows three, 10 month-old ×*Heucherella* 'Honey Rose' in bloom, in the ground, in a trial bed in the shade in October in Canby, Oreg.

DETAILED PLANT DESCRIPTION

Figure 3:
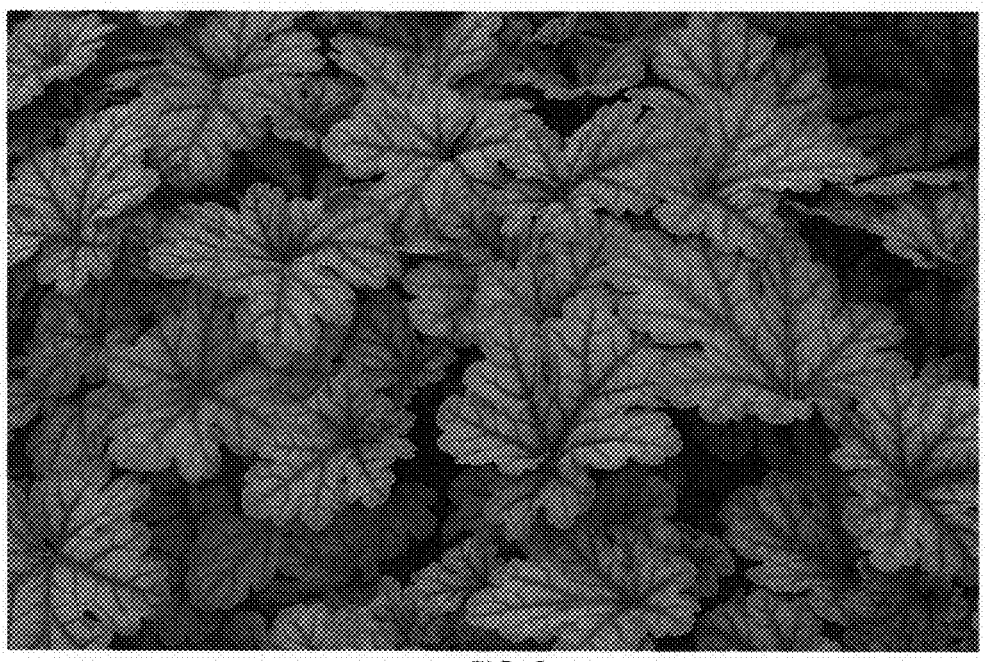
FIG. 3 shows the spring coloration on plants grown in 4 inch containers in the greenhouse in early May in Canby, Oreg.

The following is a detailed description of the new ×*Heucherella* cultivar based on observations of 10 month-old specimens growing in the ground outside in a shaded trial bed in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart*, fifth edition.

Plant:

*Form*.—Basal rosette, herbaceous perennial.
*Hardiness*.—USDA Zone 4 to 9.
*Size*.—20 cm tall from top of the foliage to the ground and 42 cm wide.
*Habit*.—Mounding.
*Vigor*.—Excellent.
*Roots*.—Fibrous, freely branching, fine, and white in color. Roots develop easily from cuttings.

Leaf:

*Type*.—Simple.
*Arrangement*.—Rosette.

*Shape*.—Ovate.

*Lobing/division*.—5 to 7 lobes palmately parted with the terminal the longest and most deeply parted, each with distinctly cut secondary lobes (the depth of the lobes varies with plant maturity and leaf age; leaves become more deeply lobed with maturity).

*Venation*.—Palmate, veins both sides Greyed Red 182C.

*Margins*.—Broadly crenate.

*Apex*.—Mucronulate.

*Base*.—Cordate, lobes usually overlapping.

*Blade size*.—Grows to 13 cm long and 11 cm wide, usually smaller.

*Surface texture*.—Glandular both surfaces.

*Petiole description*.—Grows to 18 cm long and 2 mm wide, glandular hairs, closest to Grey Brown N199B.

*Leaf color*.—Variable depending on temperature; spring, topside, Greyed Orange 174C with veins Greyed Orange 178B, bottom side closest to Greyed Purple 184A; summer topside closest to Greyed Purple 182B with the veil closest to N155A, bottom side closest to Greyed Purple 187C; fall, topside Greyed Purple 183D with the veil closest to N155A, bottom side closest to Greyed Purple 187B; winter, topside closest to Brown 200C with the veil Black 202C, bottom side closest to 182B.

Inflorescence:

*Size*.—Grows to 3 cm wide and 12 cm long.

*Type*.—Raceme.

*Number of flowers per raceme*.—About 40.

*Number of raceme*.—7.

*Peduncle*.—Grows to 27 cm tall, 2 mm wide at base, Greyed Orange 176B, glandular hairs.

*Pedicel*.—Variable, with glandular hairs, Greyed Orange 176B.

*Bloom period*.—May with sporadic rebloom in Canby, Oreg.

Flower bud:

*Size*.—2 mm wide and 3 mm long.

*Description*.—Glandular puberulent, ovoid.

*Color*.—Yellow 11D.

Flower:

*Type*.—Imperfect.

*Shape*.—Campanulate.

*Size*.—5 mm deep and 10 mm wide.

*Petal description*.—5 in number, lanceolate, 5 mm long and 1.5 mm wide, slightly reflexed, tip acuminate, base attenuate, margin entire, glabrous on both sides, White NN155D on both sides.

*Calyx description*.—5 mm deep and 5 mm wide, with 5 lobes, divided ¾ way to the base, campanulate, glandular hairs on outside, glabrous inside, tip obtuse, margin entire, NN155D on both sides.

*Stamen description*.—10 in number, 2 mm long, White NN155D overall, no pollen.

*Pistil description*.—One central two beaked pistil, 4.5 mm long and 2 mm wide, White NN155D.

*Fragrance*.—None.

*Lastingness*.—Each raceme blooms for about 2 weeks on the plant.

*Flower attitude*.—Outwards.

*Flowering stem attitude*.—Upright to semi-upright.

Fruit and seed: None.

Disease and pest tolerance: The new cultivar is typical to the genus. No known resistances to pests or diseases. No problems have been found in Canby, Oreg.

I claim:

1. A new and distinct ×*Heucherella* plant as herein illustrated and described.

* * * * *

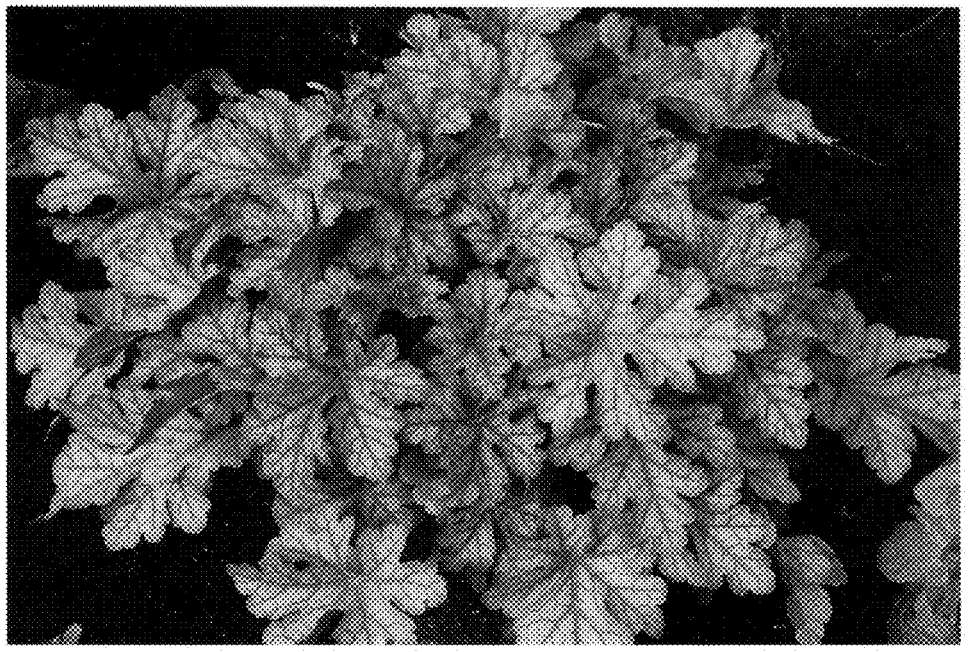
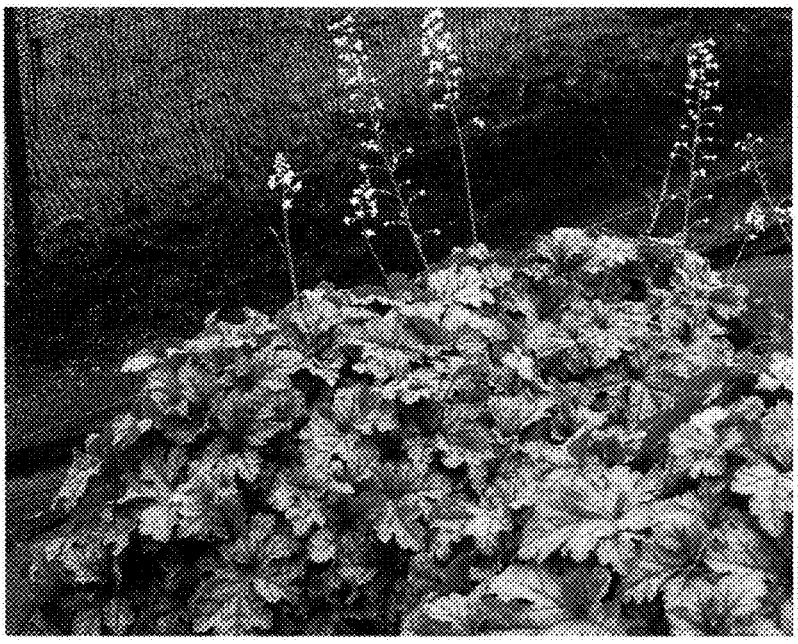
FIG. 1 above
FIG. 2 on left